(12) United States Patent
Deshpande et al.

(10) Patent No.: US 7,662,955 B2
(45) Date of Patent: Feb. 16, 2010

(54) PROCESS FOR THE PREPARATION OF CEFOXITIN

(75) Inventors: Pandurang Balwant Deshpande, Chennai (IN); Bhausaheb Pandharinath Khadangale, Chennai (IN)

(73) Assignee: Orchid Chemicals and Pharmaceuticals Ltd., Chennai (IN)

( * ) Notice: Subject to any disclaimer, the term of this patent is extended or adjusted under 35 U.S.C. 154(b) by 620 days.

(21) Appl. No.: 10/548,888

(22) PCT Filed: Dec. 31, 2003

(86) PCT No.: PCT/IB03/06239

§ 371 (c)(1),
(2), (4) Date: Jun. 27, 2006

(87) PCT Pub. No.: WO2004/083217

PCT Pub. Date: Sep. 30, 2004

(65) Prior Publication Data

US 2006/0252928 A1 Nov. 9, 2006

(30) Foreign Application Priority Data

Mar. 20, 2003 (IN) .......................... 236/MAS/2003

(51) Int. Cl.
*C07D 501/57* (2006.01)
(52) U.S. Cl. .................................................... 540/221
(58) Field of Classification Search .................. 540/221
See application file for complete search history.

(56) References Cited

U.S. PATENT DOCUMENTS

| | | | | |
|---|---|---|---|---|
| 3,994,885 A | * | 11/1976 | Koppel | 540/221 |
| 4,044,000 A | * | 8/1977 | Koppel | 540/319 |
| 4,200,576 A | * | 4/1980 | Feyen et al. | 514/201 |
| 4,217,348 A | * | 8/1980 | Treuner et al. | 514/201 |
| 4,284,767 A | * | 8/1981 | Humber et al. | 540/222 |
| 4,297,488 A | * | 10/1981 | Christensen et al. | 540/221 |
| 4,394,375 A | * | 7/1983 | Bentley et al. | 424/114 |
| 4,415,566 A | * | 11/1983 | Wetzel et al. | 514/206 |
| 4,670,431 A | * | 6/1987 | Milner | 514/194 |
| 5,162,523 A | * | 11/1992 | Keith et al. | 540/227 |
| 5,523,400 A | * | 6/1996 | Wei et al. | 514/202 |
| 6,313,289 B1 | * | 11/2001 | Ludescher et al. | 540/222 |
| 6,825,345 B2 | * | 11/2004 | Decristoforo et al. | 540/222 |
| 6,894,162 B2 | * | 5/2005 | Kremminger | 540/222 |
| 7,355,041 B2 | * | 4/2008 | Greil et al. | 540/215 |
| 7,470,786 B2 | * | 12/2008 | Datta et al. | 544/227 |
| 2007/0027314 A1 | * | 2/2007 | Manca et al. | 540/228 |
| 2008/0242858 A1 | * | 10/2008 | Parthasaradhi et al. | 540/222 |
| 2009/0093032 A1 | * | 4/2009 | Tagliani et al. | 435/118 |

FOREIGN PATENT DOCUMENTS

IN 2004CH00303 A * 6/2007
PL 156026 B1 * 5/1989
WO WO 9806723 A1 * 2/1998

OTHER PUBLICATIONS

Translation of PL156026 (1989).*

* cited by examiner

*Primary Examiner*—Mark L Berch
(74) *Attorney, Agent, or Firm*—Oliff & Berridge, PLC

(57) ABSTRACT

A process for the preparation of cefoxitin of formula (I)

(I)

The process includes treating the compound of formula (II)

(II)

with a halogenating agent in an organic solvent, followed by treatment with alkali/alkaline earth metal methoxide at a temperature in the range of −100° C. to 0° C. The product formed is then isolated as an organic amine salt of the formula (III), (III)

The salt of formula (III) is treated with a base in the presence of solvent at a temperature in the range of −75 to 10° C., the product formed is isolated as an organic amine salt of the formula (IV)

(IV)

The compound of formula (IV) is carbamoylated with isocyanate of formula (V)

RNCO (V)

in the presence of a solvent at a temperature in the range of −60° C. to 10° C., and isolating to get cefoxitin of the formula (I).

12 Claims, No Drawings

PROCESS FOR THE PREPARATION OF CEFOXITIN

FIELD OF THE INVENTION

The present invention relates to an improved process for the preparation of cefoxitin of formula (I).

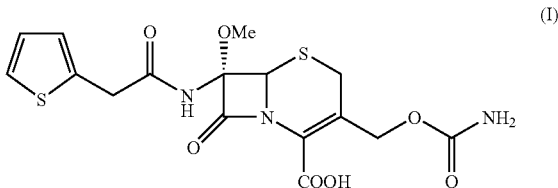

(I)

BACKGROUND OF THE INVENTION

U.S. Pat. No. 4,297,488 discloses different processes for the preparation of cefoxitin, which uses ester protected cephem nucleus. These processes involve deprotection after carbamoylation because of which, yield of the product is less.

U.S. Pat. Nos. 4,210,750 and 4,292,750 disclose a process for the preparation cefoxitin, which involve the usage of an isocyanate wherein the labile substituent is hydrocarbyl or substituted hydrocarbyl group.

The above said prior art processes always yield cefoxitin with poor quality, and color.

We have now found an improved process for the preparation of the compound of formula (I), which process has advantages over the processes described in the above-mentioned prior art documents.

OBJECTIVES OF THE INVENTION

The main objective of the present invention is to provide a process for preparation of cefoxitin of the formula (I).

Another objective of the present invention is to provide novel intermediates of formulae (III) and (IV) their use in the preparation of cefoxitin of the formula (I).

Yet another objective of the present invention is to provide the process for the preparation of cefoxitin, which is easy to implement on commercial scales.

Another objective of the present invention is to provide novel intermediates of formula (III) & (IV) for the preparation of cefoxitin.

Still another objective of the present invention is to provide a high-yielding method of producing cefoxitin of the formula (I).

SUMMARY OF THE INVENTION

Accordingly, the present invention provides an improved process for the preparation of cefoxitin of the formula (I),

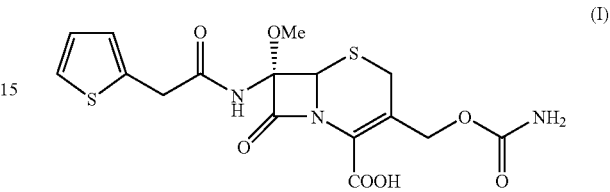

(I)

the said process comprising the steps of:
  (i) treating the compound of formula (II) with a halogenating agent in an organic solvent, followed by treatment with alkali/alkaline earth metal methoxides at a temperature in the range of −100° C. to 0° C., isolating the product formed as an organic amine salt of the formula (III), where $M^+$ represents an organic counter ion
  (ii) treating the salt of formula (III) with a base in the presence of solvent at a temperature in the range of −75 to 10° C., isolating the product formed as an organic amine salt of the formula (IV), where $M^+$ represents an organic counter ion,
  (iii) carbamoylating the compound of formula (IV) with isocyanate of formula (V) wherein R is a labile group in the presence of a solvent at a temperature in the range of −60° C. to 10° C., and isolating to get cefoxitin of the formula (1), and
  (iv) if required converting cefoxitin into cefoxitin sodium using source of sodium ion in the presence of solvent at a temperature in the range of −60° C. to 0° C.

The synthesis of cefoxitin of the formula (I) is as shown in Scheme-I:

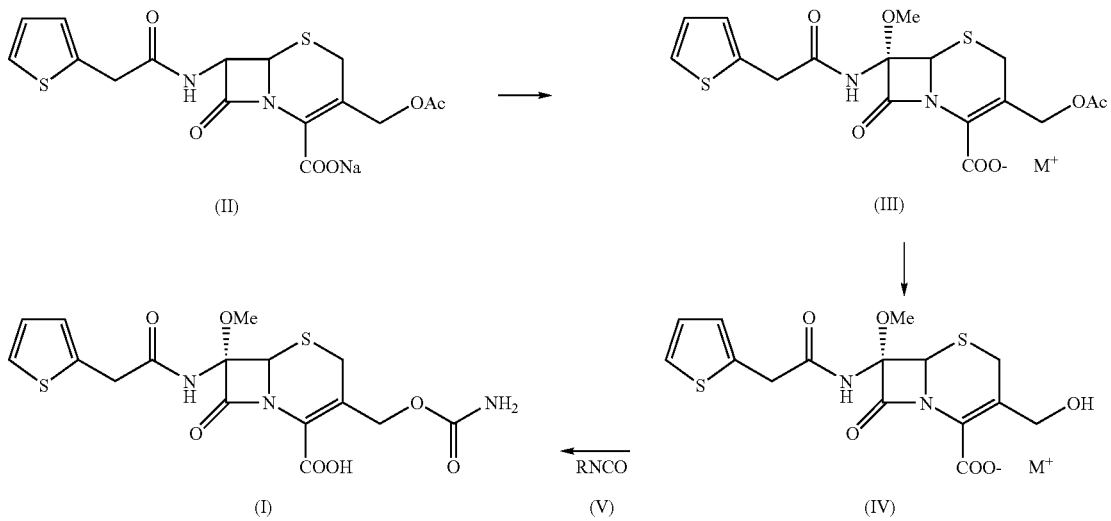

DETAILED DESCRIPTION OF THE INVENTION

In an embodiment of the present invention, the halogenating agent used in step (i) is selected form t-butoxy chloride, N-chlorosuccinimide, N-bromosuccinimide, bromine or chlorine.

In another embodiment of the present invention, the organic solvent used in step (i) is selected from dichloromethane, methanol, chloroform, THF or ethylene chloride and the like or mixtures thereof.

In another embodiment of the present invention, the organic amine used in step (i) is selected from diethylamine, methylethylamine, triethylamine, cyclohexylamine, dicyclohexylamine, N,N'-dibenzylethylenediamine, 1,8-diazabicyclo(5.4.0)undec-7-ene (DBU), 1,5-diazabicyclo(4.3.0)non-5-ene, N,N'-diphenylethylenediamine, 1,4-diazabicyclo(2.2.2)octane, N,N-diisopropylethylamine, N,N-diisopropylamine, octylamine, and the like, more particularly cyclohexyl amine salt.

In yet another embodiment of the present invention the alkali/alkaline earth metal methoxides employed in step (i) is selected from lithium methoxide, sodium methoxide, magnesium methoxide, and the like.

In still another embodiment of the present invention, the solvent employed in step (ii) is selected from methanol, acetone, water, TBF, ethyl acetate and the like or mixtures thereof; and the base employed in step (ii) is selected from sodium hydroxide, potassium hydroxide and the like, more particularly sodium hydroxide.

In another embodiment of the present invention, the organic amine used in step (ii) is selected from cyclohexylamine, dicyclohexylamine, N,N'-dibenzylethylenediamine, 1,8-diazabicyclo(5.4.0)undec-7-ene (DBU), 1,5-diazabicyclo(4.3.0)non-5-ene, N,N'-diphenylethylenediamine, 1,4-diazabicyclo(2.2.2)octane, N,N-diisopropylethylamine, N,N-diisopropylamine, octylamine, more particularly benzathine salt (N,N'-dibenzylethylenediamine).

In another embodiment of the present invention, the solvent employed in step (iii) is selected from THF, methanol, dichloromethane, acetone, ethyl acetate, methyl acetate or mixtures thereof.

In still another embodiment of the present invention, the labile group represented by R in step (iii) is selected from chlorosulphonyl, mono, di or trichloroacetyl, bromosulphonyl, trichloroethoxycarbonyl, trimethylsilyl or chlorobenzene sulphonyl group.

In yet another embodiment of the present invention, the starting material of formula (II) is prepared according to the procedures available in the prior art.

In an embodiment of the present invention, the sodium ion source used in step (iv) is such as sodium 2-ethyl hexonate, sodium acetate, sodium lactate and the like.

In an embodiment of the present invention, the solvent used in used in step (iv) is selected from methanol, acetone, THF, ethyl acetate, acetonitrle, isobutyl methyl ketone, ethyl methyl ketone, water and the like or mixtures thereof more particularly, acetone/methanol.

In still another embodiment of the present invention cefoxitin sodium may be washed with solvents like methanol, acetone, IPE, ethyl acetate, hexane, toluene and the like or mixtures thereof.

The foregoing technique has been found to be markedly attractive, both from commercial point of view and affords good quality of cefoxitin of formula (I).

The present invention is illustrated with the following examples, which should not be construed as limiting the scope of the invention.

EXAMPLE I

Step i: Preparation of 7-$\alpha$-methoxy-7-(2-thienyl)acetamidocephalosporanic Acid Cyclohexyl Amine Salt To dichloromethane (806 ml) and methanol (83.0 ml), 7-(2-thienyl) acetamidocephalosporanic acid sodium salt (100 gm) was added and cooled to −20° C. Methane sulfonic acid (25.3 gm) was added and cooled to −90° C. N-Chlorosuccinimide (60.8 gm) was added followed by sodium methoxide solution (337.3 gm) in methanol (160 ml) was added slowly at −90° C. The reaction mass was stirred till completion of reaction, after completion of reaction sodium metabisulphite (20.6 gm), aqueous acetic acid (150 ml) and sodium chloride solution (189 gm in 1164 ml water) were added at −90° C. After addition, 1:1 HCl (23.5 ml) was added at 0° C., then the layers were separated, organic layer was washed with water and distilled of organic layer until final volume becomes (500 ml). To this mass cyclohexyl amine in acetone was added dropwise till pH becomes 6.5. IPE was added and stirred the reaction mass for 2 hours at 0° C. The solid obtained was filtered, washed with acetone and dried to get the title compound (101.0 gm).

Step ii: Preparation of 3-hydroxymethyl-7-$\alpha$-methoxy-7-[(2-thienyl)acetamido]-3-cephem-4-carboxylic acid N,N'-bis(phenylmethyl)-1,2-ethanediamine Salt To a mixture of DM water (326 ml) and methanol (366 ml), 7-$\alpha$-methoxy cephalothin (100 gm) obtained from step (ii) was added at 1° C. and cooled to −45° C. To the reaction mixture, sodium hydroxide solution (28 gm in 167 ml water) was added slowly at 5° C. and stirred at −45° C. till completion of reaction. After completion of reaction, pH was adjusted to 7.0 using aqueous acetic acid at −45° C. The temperature of the reaction mass was raised to 28° C. and distilled of approximately 400 ml reaction mass. Ethyl acetate (52 ml), benzathine diacetate (40 gm) were added and stirred the reaction mixture for 2 hour at 20° C. The reaction mass was cooled and the solid obtained was filtered, washed with water followed by ethyl acetate and dried to get the title compound (72 gm).

Step iii: Preparation of 7-$\alpha$-methoxy-7-[(2-thienyl)acetamido]-3-caramoyloxymethyl-3-cephem-4-carboxylic Acid To THF (400 ml) decarbomoyl cefoxitin benzathine salt (50 gm) obtained from step (iii) was added, and cooled to −55° C., followed by slow addition of precooled solution of chloro sulphonyl isocynate (35.0 gm) in THF (50 ml) at −55° C. Reaction mass was stirred till completion of the reaction. After completion of the reaction, the reaction mass was added into cold DM water and stirred for 2 hours. Ethyl acetate (1277.0 ml) was added; the byproduct obtained was filtered and washed with ethyl acetate/water mixture. To the filtrate 10% sodium chloride solution (225 ml) was added, stirred 10 minutes, then the layer were separated. The organic layer was washed with 10% sodium chloride solution. The product was extracted with mixture of sodium bicarbonate solution and sodium chloride solution. The pH of aqueous solution was adjusted to 2.0 with 1:1 HCl and cooled to 10° C. The solid obtained was filtered, washed, and dried. The dried solid was added to DM water (462 ml) at 25° C. pH of reaction mass was adjusted to 6.0 with sodium carbonate solution (83 ml) and degassed for 30 minutes. Acetic acid was added to adjust the pH to 5.4-5.6, and activated carbon (3.5 gm) was added and stirred for 10 minutes. Carbon was filtered and washed the bed with water. To the filtrate ethyl acetate (9 ml) was added and pH of filtrate adjusted to 2.0 with 1:1 HCl (14 ml).

The reaction mass cooled to 10° C., the solid obtained was filtered, washed with water, and dried to yield title compound in pure form.

EXAMPLE II

Preparation of Cefoxitin Sodium:

To cefoxitin acid (11 g) in 12% aqueous acetone (88 ml), 60% aqueous sodium lactate (4.7 g) solution was added at 30° C. and stirred for 10 minutes, excess acetone was added (275 ml) to precipitate the product. The solid was filtered and dried under vacuum to yield the title compound in pure form (10 g)

EXAMPLE III

Preparation of Cefoxitin Sodium:

To cefoxitin acid (25 g) in a mixture of acetone (350 ml) and methanol (87 ml), sodium 2-ethyl hexonate (10.7 g) in acetone (60 ml) was added at 20° C. and stirred for 30 minutes. The reaction mass was cooled to 10° C. to precipitate the product. The solid was filtered and dried under vacuum to yield the title compound in pure form.

We claim:

1. A process for the preparation of cefoxitin of formula (I)

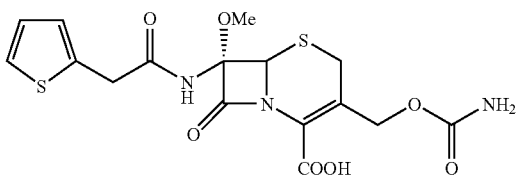
(I)

the process comprising:
(i) treating a compound of formula (II)

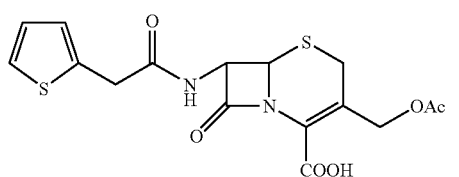
(II)

wherein Ac represents acetyl, with a halogenating agent in an organic solvent, followed by treatment with an alkali/alkaline earth metal methoxide at a temperature in the range of −100° C. to 0° C., isolating the product formed as an organic amine salt of the formula (III), where $M^+$ represents an organic ammonium ion and Ac is as defined above;

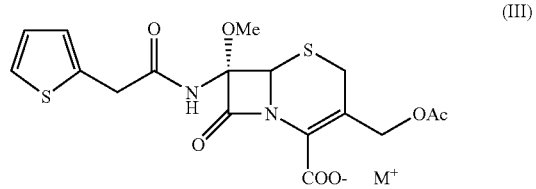
(III)

(ii) treating the salt of formula (III) with a base in the presence of a solvent at a temperature in the range of −75 to 10° C., isolating the product formed as an organic amine salt of formula (IV), where $M^+$ represents an organic ammonium ion,

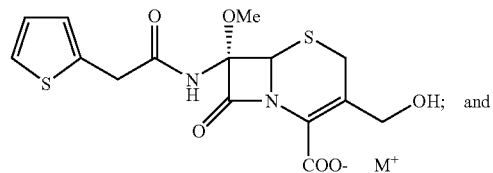
(IV)

(iii) carbamoylating the compound of formula (IV) with an isocyanate of formula (V)

RNCO  (V)

wherein R is a labile group selected from chlorosulphonyl, mono-, di- or tri-chloroacetyl, bromosulphonyl, trichloroethoxycarbonyl, trimethylsilyl or chlorobenzene sulphonyl, in the presence of a solvent at a temperature in the range of −60° C. to 10° C., and isolating to get cefoxitin of formula (I).

2. The process of claim 1, wherein the halogenting agent in step (i) is t-butoxy chloride, N-chlorosuccinimide, N-bromosuccinimide, bromine or chlorine.

3. The process of claim 1, wherein the organic solvent in step (i) is dichloromethane, methanol chloroform, THF, ethylene chloride or a mixture thereof.

4. The process of claim 1, wherein the organic amine in step (i) is diethylamine, methylethylamine, triethylamine, cyclohexylamine, dicyclohexylamine, N,N'-dibenzylethylenediamine, 1,8-diazabicyclo(5.4.0)undec-7-ene (DBU), 1,5-diazabicyclo(4.3.0)non-5-ene, N,N'-diphenylethylenediamine, 1,4-dizabicyclo(2.2.2)octane, N,N-diisopropylethylamine, N,N-diisopropylamine or octylamine.

5. The process of claim 1, wherein the alkali/alkaline earth metal methoxide in step (i) is lithium methoxide, sodium methoxide or magnesium methoxide.

6. The process of claim 1, wherein the solvent in step (ii) is methanol, acetone, water, THF, ethyl acetate or a mixture thereof.

7. The process of claim 1, wherein the base in step (ii) is sodium hydroxide or potassium hydroxide.

8. The process of claim 1, wherein the organic amine in step (ii) is cyclohexylamine, dicyclohexylamine, N,N'-dibenzylethylenediamine, 1,8-diazabicyclo(5.4.0)undec-7-ene (DBU), 1,5-diazabicyclo(4.3.0)non-5-ene, N,N'-diphenylethylenediamine, 1,4-dizabicyclo(2.2.2)octane, N,N-diisopropylethylamine, N,N-diisopropylamine or octylamine.

9. The process of claim 1, wherein the solvent in step (iii) is THF, methanol dichloromethane, acetone, ethyl acetate, methyl acetate or a mixture thereof.

10. A compound of formula (III)

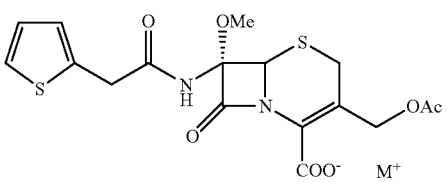
(III)

where $M^+$ represents cyclohexylammonium and Ac is acetyl.

11. A compound of formula (IV)

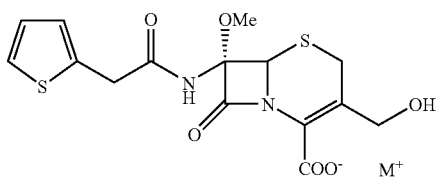

where M⁺ represents N,N'-dibenzylethylenediammonium.

12. A process for the preparation of cefoxitin sodium, the process comprising
(i) treating a compound of formula (II)

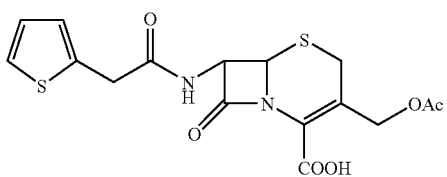

wherein Ac represents acetyl, with a halogenating agent in an organic solvent, followed by treatment with an alkali/alkaline earth metal methoxide at a temperature in the range of −100° C. to 0° C., isolating the product formed as an organic amine salt of the formula (III), where M⁺ represents an organic ammonium ion and Ac is as defined above;

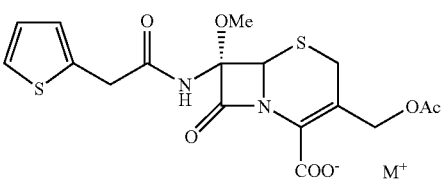

(ii) treating the salt of formula (III) with a base in the presence of a solvent at a temperature in the range of −75 to 10° C., isolating the product formed as an organic amine salt of formula (IV), where M⁺ represents an organic ammonium ion,

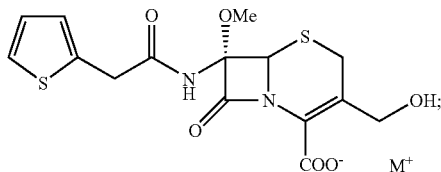

(iii) carbamoylating the compound of formula (IV) with an isocyanate of formula (V)

$$RNCO \quad (V)$$

wherein R is a labile group selected from chlorosulphonyl, mono-, di- or tri-chloroacetyl, bromosulphonyl, trichloroethoxycarbonyl, trimethylsilyl or chlorobenzene sulphonyl, in the presence of a solvent at a temperature in the range of −60° C. to 10° C., and isolating to get cefoxitin of formula (I)

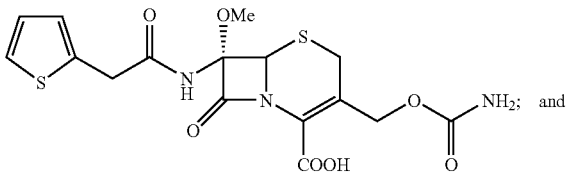

(iv) converting the cefoxitin into cefoxitin sodium using a source of sodium ion in the presence of solvent at a temperature in the range of −60° C. to 0° C.

* * * * *